United States Patent [19]

Forsyth et al.

[11] 4,031,249
[45] June 21, 1977

[54] COMPOSITIONS CONTAINING CERTAIN 2,4-HALO-6-NITROPHENOLS OR DERIVATIVES THEREOF AND METHODS FOR USING SAME TO ERADICATE INTERNAL PARASITES IN WARM-BLOODED ANIMALS

[75] Inventors: Bruce Adam Forsyth, Croydon; David Ernest Pryor, Balwyn; Errol James McGarry, Bundoora; Donald William Gerald Harney, Doncaster, all of Australia

[73] Assignee: ICI Australia Limited, Melbourne, Australia

[22] Filed: May 19, 1975

[21] Appl. No.: 578,811

[30] Foreign Application Priority Data

June 7, 1974   Australia ............................ 7826/74
Apr. 7, 1975   Australia ............................ 1153/75

[52] U.S. Cl. ........................... 424/347; 260/622 R
[51] Int. Cl.$^2$ ............... A61K 31/055; C07C 79/22
[58] Field of Search ................. 424/347; 260/622 R

[56] References Cited
UNITED STATES PATENTS 2,344,489   11/1975   Boyer et al. ..................... 260/622
3,108,927   10/1963   Pyne ................................. 424/347
3,465,084   9/1969    Jackson .......................... 424/347

OTHER PUBLICATIONS

Kalina—Chem. Abst. vol. 79 (1973), p. 18366q.
Sekomura et al.—Chem. Abst. vol. 79, (1973) p. 28389p.
Stanek et al.—Chem. Abst., vol. 59, (1963) pp. 21136h & 2114d.

Primary Examiner—Sam Rosen
Attorney, Agent, or Firm—Cushman, Darby & Cushman

[57] ABSTRACT

A composition of matter for treating warm-blooded animals to eradicate internal parasites comprising a compound chosen from the group consisting of 2,4-dibromo-6-nitrophenol
2,4-dichloro-6-nitrophenol
2-chloro-4-fluoro-6-nitrophenol
2-bromo-4-fluoro-6-nitrophenol
2-iodo-4-fluoro-6-nitrophenol
2-bromo-4-chloro-6-nitrophenol and phenolic derivatives thereof and an inert carrier therefor. The composition is particularly useful in killing trematodes or nematodes.

10 Claims, No Drawings

COMPOSITIONS CONTAINING CERTAIN 2,4-HALO-6-NITROPHENOLS OR DERIVATIVES THEREOF AND METHODS FOR USING SAME TO ERADICATE INTERNAL PARASITES IN WARM-BLOODED ANIMALS

This invention relates to compositions for killing internal parasites of warm blooded animals; in particular it relates to compositions for killing trematodes or nematodes. An example of a trematode is the liver fluke (*Fasciola hepatica*) which is a parasite of bile ducts of the liver of ruminants, such as cattle, sheep and goats. The liver fluke each year causes a significant amount of economic loss, not only from the death of the host animal but also from the deterioration in the value of meat and wool produced by infected animals. In cattle a loss in milk yield from liver fluke infection will also occur and in addition the loss sustained by the condemnation of infected livers as human food may also be considerable. An example of a nematode is *Haemonchus contortus* which is a nematode parasitic in the abomasum or fourth stomach of ruminants. It is a blood sucking parasite and when present in large numbers can cause anaemia and finally the death of the host. It can cause extensive losses, but only in the value of the animals which it may kill but also in the diminished production of commercial items such as wool and meat. There is therefore a commercial need to treat animals with chemicals which are both safe and effective in reducing the incidence and severity of diseases caused by both trematodes and nematodes.

We have now found a class of compounds which are effective in killing liver fluke.

Accordingly we provide a composition of matter for treatment of animals comprising a compound chosen from the group consisting of 2,4-dibromo-6-nitrophenol
2,4-dichloro-6-nitrophenol
2-chloro-4-fluoro-6-nitrophenol
2-bromo-4-fluoro-6-nitrophenol
2-iodo-4-fluoro-6-nitrophenol
2-bromo-4-chloro-6-nitrophenol and phenolic derivatives thereof and an inert carrier therefor.

For convenience of application we prefer that the phenols are not present as the free phenol but are in the derivative form, conveniently as a salt of a non-toxic base such as for example an alkali metal hydroxide or alkaline earth metal hydroxide, amines such as, e.g., triethanolamine N-methylglutamine or ammonia. The purpose of the salt is merely to increase the solubility of the active ingredient in aqueous formulations.

The nature of the phenolic derivatives is not narrowly critical. Thus the derivatives may be for example a salt of the phenol or it may be a derivative wherein the hydrogen atom of the phenolic group is substituted with an alkyl, alkenyl or acyl group each containing 1–6 l carbon atoms.

Compounds in which the phenolic group is substituted with a polar group such as carboxylic acid or an amine or a quaternary ammonium salt are particularly preferred. Examples of preferred substituents on the phenolic group are as follows $$-\overset{O}{\underset{\|}{C}}-CH=CH-CO_2H, \quad -\overset{O}{\underset{\|}{C}}-alkylene-NR_2, \quad -\overset{O}{\underset{\|}{C}}-OR$$

-continued

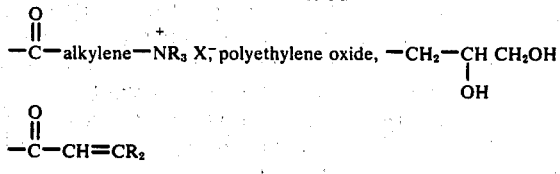

$$-\overset{O}{\underset{\|}{C}}-CH=CR_2$$

wherein R = H or an alkyl group containing from one to six carbon atoms.

Certain of the compounds are novel. These novel compounds per se are part of our invention. The novel compounds are

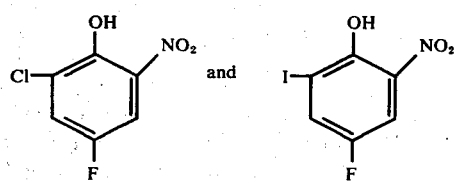

The compounds may be prepared by methods obvious to those skilled in the art for the synthesis of substituted phenols.

The compounds may be made by nitration of the corresponding 2,4-dihalo phenol. Alternatively, the 4-halo phenol may be nitrated and the 2-position halogenated with, e.g. iodine and potassium iodate: In a further method one of the halo groups of a dihalo nitro phenol may be replaced with a different halo group. Group R may be introduced into the phenols by methods analogous to those known for the unhalogenated or unnitrated phenols.

We also provide a method of treating warm blooded animals to eradicate certain internal parasites; such method comprises administering to said warm blooded animals a therapeutic dose of a composition comprising as active ingredient a compound as listed hereinbefore.

The compositions are of particular use for the treatment of *Fasciola sp* such as for example *Fasciola hepatica* and *Fasciola gigantica*.

For effective treatment, certain dosage levels are desired depending upon the compound employed, the type of animal to be treated, and the particular helminth being combatted. In general, effective fluke efficacy is achieved when the composition is administered in a single dose at dosage levels of from about 1 to 50 mg active ingredient/kg of animal body weight, and preferably from about 3 to 20 mg active ingredient per kg of animal body weight.

The composition of the present invention may be administered in a variety of ways, depending upon the particular animal employed, the type of anthelminitic treatment normally given to such an animal, the materials employed, and the particular helminths being combatted. It is preferred to administer them in a single efficacious oral or parenteral dose at a time when fluke or nematode infection is apparent or suspected. They may be employed alone or in combination with other anthelmintics, parasiticides or antibacterials. The compounds may also be applied as a "pour on" formulation for dermal application. The amounts of the active anthelmintic ingredient in the composition, as well as the remaining constituents are varied according to the type of treatment to be employed, the host animal, and the particular parasitic disease being treated. In general, however, compositions containing a total weight percent of the active compound or compounds ranging from 0.001 to 95% will be suitable with the remainder being any suitable carrier or vehicle. Furthermore, the compositions should contain enough of the active ingredient to provide an effective dosage for the proper treatment of the parasitic disease.

A number of modes of treatment may be employed, and each to some extent determines the general nature of the composition. For example, the anthelmintic compositions may be administered to domesticated animals in single unit oral dosage form such as a tablet, bolus, capsule or drench; in a liquid form suitable for parenteral administration; or they may be compounded as feed premix to be later admixed with the animal's food.

When the compositions are to be solid unit dosage forms as in tablets, capsules, or boluses, the ingredients other than the active ingredient may be any other pharmaceutically acceptable vehicles convenient in the preparation of such forms, and preferably materials nutritionally suitable such as starch, lactose, talc, magnesium stearate, vegetable gums, and the like. Moreover when capsules are employed, the active compound may be used in essentially undiluted form, the only extraneous material being that of the capsule casing itself which may be hard or soft gelatin or any other pharmaceutically acceptable encapsulating material. When the dosage form is to be used for parenteral administration, the active material is suitably admixed with an acceptable base vehicle. In all of such forms, i.e. in tablets, boluses, capsules, and injectable formulations, the active compound conveniently ranges from about 5 to 80% by weight of the total composition.

When the unit dosage form is to be in the form of a drench, the active ingredient may be mixed with agents which will aid in the subsequent suspending of the active compound in water, such as bentonite, clays, water-soluble starch, cellulose derivatives, gums, surface active agents and the like to form a dry predrench composition, and this predrench composition added to water just before use. In the predrench formulation, in addition to the suspending agent, such ingredients as preservatives, antifoam compounds, and the like may be employed. Such a dry product may contain as much as 95% by weight of the active compound, the rest being contributed by the excipients. Preferably, the solid composition contains from 30% to 95% by weight of the active compound. Enough water should be added to the solid product to provide the proper dosage level within a convenient amount of liquid for a single oral dose. Liquid drench formulations containing from about 10 to 50 weight percent of dry ingredients will in general be suitable with the preferred range being from 15 to 30 weight percent. Where the compositions are intended to be used as feeds, feed supplements, or feed premixes, they will be mixed with suitable ingredients of an animal's nutrient ration. The solid orally-ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antiobiotic mycelia, soya grits, crushed limestone and the like are all suitable. The active compounds are intimately dispersed or admixed throughout the solid inert carrier by methods such as grinding, stirring, milling or tumbling. By selecting proper diluents and by altering the ratio of carrier to active ingredient, compositions of any desired concentration may be prepared. Feed supplement formulations containing from about 10 to 30% by weight of active ingredient are particularly suitable for addition to feeds. The active compound is normally dispersed or mixed uniformly in the diluent but in some instances may be absorbed on the carrier.

These supplements are added to the finished animal feed in an amount adequate to give the final concentration of active ingredient desired for controlling or treating the helminth infection by way of the animal ration. Although the preferred level in feeds will depend on the particular compounds being employed, the active ingredients of this invention are normally fed at levels of 0.05–25% in the feed. As stated above, animals are preferably treated at a time when the infestation is apparent or suspected and the most preferred method for such treatment is via the single oral dose technique. Thus administration of medicated feed is not preferred but may certainly be employed. Similarly, the amounts of drug present in the feed may be reduced to levels in the order of 0.001% to 3.0 weight percent based on the weight of feed, and the medicated feed administered over prolonged periods. This would be in the nature of a preventive or propylactic measure but again is not the mode of choice. Another method of administering the compositions of this invention to animals whose feeds are conveniently pelleted, such as sheep, is to incorporate them directly in the pellets. For instance, the compositions are readily incorporated in nutritionally adequate alfalfa pellets at levels of 2 to 110 grams per pound of pellets for therapeutic use, and at lower levels for example 80 to 1000 milligrams per pound for prophylactic use, and such pellets fed to the animals. The compositions may also optionally contain other drugs of veterinary utility. Veterinary drugs which may be present in the veterinary compositions of this invention, depending upon the mode of administration of the said compositions, include for example, piperazine, 1-diethyl-carbamyl-4-methyl-piperazine, tetrachloroethylene, organic and inorganic arsenical compounds, tetramisole, 2-phenyl-benzimidazole, thiabendazole, phenothiazine, mebendazole and pyrantel salts.

Preferably the compositions are administered to the animal by parenteral dose and in a further aspect of our invention we provide an injectable composition comprising a sterile aqueous solution containing from 5 to 70% w/w preferably 5 to 50% w/w of the active ingredient.

The composition may be sterilized by methods known to those skilled in the art for the sterilization of injectable solution such as, for example, ultra filtration or gamma radiation.

The invention is now illustrated by, but by no means limited to, the following examples in which all parts are part by weight unless otherwise specified.

EXAMPLE 1

Preparation of 2,4-Dichloro-6-mitrophenol

Concentrated nitric acid (70%, 100 ml) was added dropwise to a cooled solution of 2,4-dichloro-6-nitrophenol (82 g) in acetic acid (300 ml). A yellow crystalline precipitate formed after approximately 5 minutes. The mixture was stirred at room temperature for 1 hour and was then poured into iced water (2 l). The yellow solid was filtered and crystallised from ethanol to give 2,4-dichloro-6-nitrophenol (72.9 g), m.p. 124°.

The following phenols were prepared by a similar procedure:

| Phenol | m.p. | Ref. |
|---|---|---|
| 2,4-Difluoro-6-nitrophenol | 48–48.5° | |
| 2-chloro-4-fluoro-6-nitrophenol | 70° | |
| 2-bromo-4-fluoro-6-nitrophenol | 67° | 1 |
| 2-fluoro-4-chloro-6-nitrophenol | 60° | |
| 2-bromo-4-chloro-6-nitrophenol | 126° | 2 |
| 4-chloro-2-iodo-6-nitrophenol | 84° | 3 |
| 4-bromo-2-chloro-6-nitrophenol | 111° | 4 |
| 4-bromo-2-iodo-6-nitrophenol | 97° | |
| 2,4-dibromo-6-nitrophenol | 116–117° | |

References
1. L.C. Raiford and A.L. LeRosen, J. Am. Chem. Soc., 1944, 66, 1872.
2. M Kohn and D Krasso, J. Org. Chem., 1946, 11, 641.
3. L.C. Raiford and G.R. Miller, J. Am. Chem. Soc., 1933, 55, 2125.
4. This compound was used as an intermediate in the preparation of nematocidal phenyl sulphonates (Chem. Abst., 1967, 67, 64043 g).

EXAMPLE 2

Preparation of 4-fluoro-2-iodo-6-nitrophenol

Concentrated nitric acid (70%, 3.5 g) was added dropwise over 10 minutes to a cooled solution of 4-fluorophenol (4 g) in acetic acid (40 ml). The mixture was stirred for a further 10 minutes and was then poured into iced water to give a yellow solid which crystallised from ethanol as bright yellow needles of 4-fluoro-2-nitrophenol (4.3 g), m.p. 72°.

A slurry of 4-fluoro-2-nitrophenol (3.3 g), sodium hydroxide (0.83 g), potassium iodide (2.33 g) and potassium iodate (1.5 g) in water (21 ml) was added to a stirred mixture of ethanol (16 ml), water (3.5 ml) and concentrated sulphuric acid (1.7 ml) at 50°. The mixture was heated under reflux for 2 hours and was then allowed to stand at room temperature overnight. A small quantity of sodium sulphite was added to decolourise the product and the yellow solid was filtered and crystallised from aqueous ethanol to give yellow crystals of 4-fluoro-2-iodo-6-nitrophenol (3.5 g) m.p. 40°.

EXAMPLE 3

Preparation of 2-fluoro-4-iodo-6-nitrophenol

Sodium nitrate (4.3 g) was added in portions over 1 hour to a solution of 2-fluoro-4,6-diiodophenol (16.3 g) in acetic acid (100 ml). The mixture was stirred for a further 15 minutes and was then poured into ice water (250 ml). The aqueous solution was concentrated under reduced pressure, extracted with chloroform and the organic solvent removed under reduced pressure. The residue was steam distilled to give 2-fluoro-4-iodo-6-nitrophenol which crystallised from aqueous ethanol (1.8 g) m.p. 96°.

4-bromo-2-fluoro-6-nitrophenol, m.p. 62° was prepared by the same procedure from 2,4-dibromo-6-fluorophenol.

EXAMPLE 4

Preparation of 2,4-dichloro-6-nitrophenyl crotonate

Crotonyl chloride (7 ml) was added to a solution of 2,4-dichloro-6-nitrophenol (10.3 g) in methylene chloride (20 ml) and the mixture was heated under reflux for 12 hours. The solution was diluted with further methylene chloride (200 ml) and extracted several times with a 10% sodium hydroxide solution. The organic layer was washed with water dried (Na$_2$SO$_4$) and the solvent removed under reduced pressure to give a pale brown oil which crystallised on standing for 24 hours 2,4-dichloro-6-nitrophenyl crotonate melted at <60°.

EXAMPLE 5

Preparation of 2,4-dichloro-6-nitrophenyl-methyl carbonate

Methyl chloroformate (1.89 g) in acetone (10 ml) was added all at once to a mixture of 2,4-dichloro-6-nitrophenol (4.16 g) and anhydrous potassium carbonate (2.76 g) in acetone (100 ml) and the mixture was heated under reflux for 2 hours. During this period the solution changed from deep red to a pale orange. The mixture was cooled, the inorganic material was filtered and washed with acetone and the solution was evaporated under reduced pressure to give a pale orange solid which crystallised from petroleum spirit (40°–60°) as colourless prisms of 2,4-dichloro-6-nitrophenyl methyl carbonate (3.5 g) m.p. 60°–61°.

The ethyl carbonate was prepared by the same procedure, m.p. 46°.

The isobutyl carbonate prepared by the same procedure was obtained as an off white oil.

EXAMPLE 6

2,4-dibromo-6-nitrophenyl was formulated as a 5% w/v aqueous solution in 5% w/v aqueous triethanolamine.

EXAMPLE 7

2,4-dichloro-6-nitrophenol was formulated as a 5% w/v aqueous solution in 5% w/v aqueous triethanolamine.

EXAMPLE 8

A volume of the solution in example 6 was injected into one sheep which was parasitised with adult *Fasciola hepatica* at a dose rate of 25 mg. of 2,4-dibromo-6-nitrophenol per kilogram body weight.

Samples of faeces were drawn before dosing and at days 7 and 11 after dosing and the number of fluke eggs per gram of faeces was estimated. The sheep was then slaughtered and the liver examined for liver fluke. The results are as follows: Fluke eggs/gram faeces:

before dosing — 240
7 days after dosing — 40
11 days after dosing — 0
Number of fluke left in liver at P.M. — 15

This compound thus shows activity against adult liver fluke which is not complete at the dose rate employed.

EXAMPLE 9

2,4-dichloro-6-nitrophenol was injected into three sheep at the dose rates shown below by injecting the calculated volume of solution from example 7. Faecal egg counts were carried out as in example 3 and the livers' were examined at post-mortem. The results are tabulated below:

| Dose rate mg/kg | Egg count | | | No of fluke at P.M. on Day 20 |
|---|---|---|---|---|
| | Day 0 | Day 7 | Day 9 | |
| 25 | 340 | 20 | 10 | 0 |
| 25 | 890 | 10 | 0 | 0 |
| 12½ | 930 | 30 | 0 | 1 |

Thus the compound is almost 100% active against adult *Fasciola hepatica* at a dose as low as 12.5 mg/kg.

EXAMPLE 10

Example 9 was repeated with the compounds listed below. The results are shown in the table.

BIOLOGICAL RESULTS

| Compound | Dose mg/kg s/c | Egg count (day) | P.M. at day 20 |
|---|---|---|---|
| 2-F, 6-NO₂, 4-F phenol | 12.5 | 380(0), 270(5), 440(7), 150(14) | — |
| 2-Cl, 6-NO₂, 4-F phenol | 12.5 | 160(0), 70(3) 0(7), 0(17) | 0 |
| 2-Br, 6-NO₂, 4-F phenol | 12.5 | 160(0), 0(3), 0(7), 0(12) | 1 |
| 2-I, 6-NO₂, 4-F phenol | 12.5 | 180(0), 80(3), 0(7), 0(12) | 0 |
| 2-F, 6-NO₂, 4-Cl phenol | 12.5 | 200(0), 140(3), 170(7), 430(12) | — |
| 2-Br, 6-NO₂, 4-Cl phenol | 12.5 | 50(0), 0(14) | 0 |
| 2-I, 6-NO₂, 4-Cl phenol | 12.5 | 190(0), 260(14) | — |
| 2-F, 6-NO₂, 4-Br phenol | 12.5 | 270(0), 280(2), 340(7), 310(14) | — |

-continued
BIOLOGICAL RESULTS
| Compound | Dose mg/kg s/c | Egg count (day) | P.M. at day 20 |
|---|---|---|---|
| 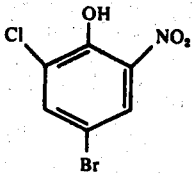 | 12.5 | 110(0), 130(14) | |
| 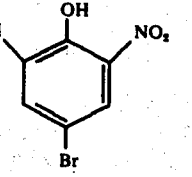 | 12.5 | 280(0), 350(2), 270(7), 170(14) | |
| 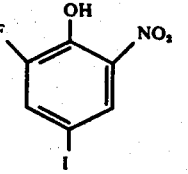 | 12.5 | 180(0), 510(2) 660(6) | |
| 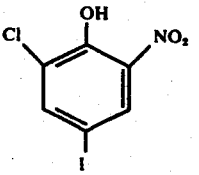 | 12.5 | 130(0), 150(7), 280(14) | |
| 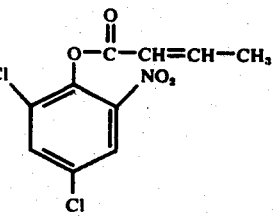 | 12.5 | 40(0), 0(12), 200(0), 0(14) | |
| 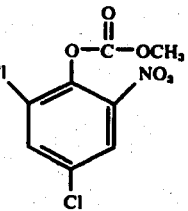 | 12.5 | 280(0), 570(3), 420(7), 0(14) | |
| 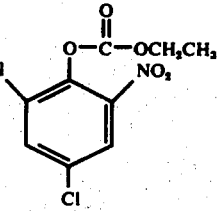 | 12.5 | 990(0), 60(3) 0(7), 30(13), 0(21) | 0 |
| 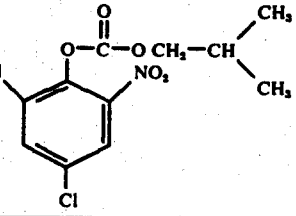 | 12.5 | 150(0), 0(14) | |

We claim:
1. A compound chosen from the group consisting of 2-chloro-4-fluoro-6-nitrophenol and salts thereof with non-toxic bases.
2. A compound chosen from the group consisting of 2-iodo-4-fluoro-6-nitrophenol and salts thereof with non-toxic bases.
3. A method of treating warm blooded animals to eradicate trematodes and nematodes; which method comprises administering to warm blooded animal in need of such treatment an effective amount of a compound selected from the group consisting of
2,4-dibromo-6-nitrophenol
2,4-dichloro-6-nitrophenol
2-chloro-4-fluoro-6-nitrophenol
2-bromo-4-fluoro-6-nitrophenol
2-iodo-4-fluoro-6-nitrophenol
2-bromo-4-chloro-6-nitrophenol
and salts thereof with a non-toxic base.
4. A method according to claim 3 wherein the compound is administered in a single dose at dosage levels of from 1 to 50 mg active ingredient/kg of animal body weight.
5. A method according to claim 4 wherein the dosage level is from 3 to 20 mg active ingredient/kg of animal body weight.
6. A method according to claim 3 wherein the compound is applied dermally as a pour on.
7. A method according to claim 3 wherein the compound is applied by injection.
8. A method according to claim 3 wherein the compound is applied as a drench.
9. A method according to claim 3 wherein the parasite is *Fasciola sp*.
10. A method according to claim 3 wherein said compound is 2-chloro-4-fluoro-6-nitrophenol, 2-iodo-4-fluoro-6-nitrophenol or salts thereof with a nontoxic base.